United States Patent [19]

Burr et al.

[11] Patent Number: 4,582,517

[45] Date of Patent: Apr. 15, 1986

[54] SEPARATION OF ETHANE AND HIGHER HYDROCARBONS FROM NATURAL GAS

[75] Inventors: Peter Burr, Munich; Peter Grimm, Hohenschaftlarn, both of Fed. Rep. of Germany

[73] Assignee: Linde Aktiengesellschaft, Wiesbaden, Fed. Rep. of Germany

[21] Appl. No.: 613,133

[22] Filed: May 23, 1984

[30] Foreign Application Priority Data

Jun. 1, 1983 [DE] Fed. Rep. of Germany ....... 3319986

[51] Int. Cl.[4] .............................................. F25J 3/02
[52] U.S. Cl. ......................................... 62/24; 62/26; 62/28; 62/30; 62/31
[58] Field of Search ................... 62/11, 23, 24, 25, 26, 62/27, 28, 29, 30, 31, 32, 36, 42, 44

[56] References Cited

U.S. PATENT DOCUMENTS

| | | | |
|---|---|---|---|
| 3,292,380 | 12/1966 | Bucklin | 62/23 |
| 3,407,613 | 10/1968 | Muller et al. | 62/26 |
| 3,596,473 | 8/1971 | Streich | 62/28 |
| 4,128,410 | 12/1978 | Bacon | 62/28 |
| 4,257,794 | 3/1981 | Shirokov et al. | 62/28 |
| 4,312,652 | 1/1982 | Mikulla | 62/32 |

Primary Examiner—S. Leon Bashore
Assistant Examiner—Andrew J. Anderson
Attorney, Agent, or Firm—Millen & White

[57] ABSTRACT

Ethane and higher hydrocarbons are separated by rectification from natural gas under elevated pressure. To obtain higher ethane yields, even for gases poor in ethane, an open mixture cycle with multistage fractional condensation is employed for the production of cold. One part of the thus-obtained condensates are introduced into the rectifying column to obtain the $C_{2+}$ hydrocarbons and the other part is recirculated to provide the required cold.

14 Claims, 1 Drawing Figure

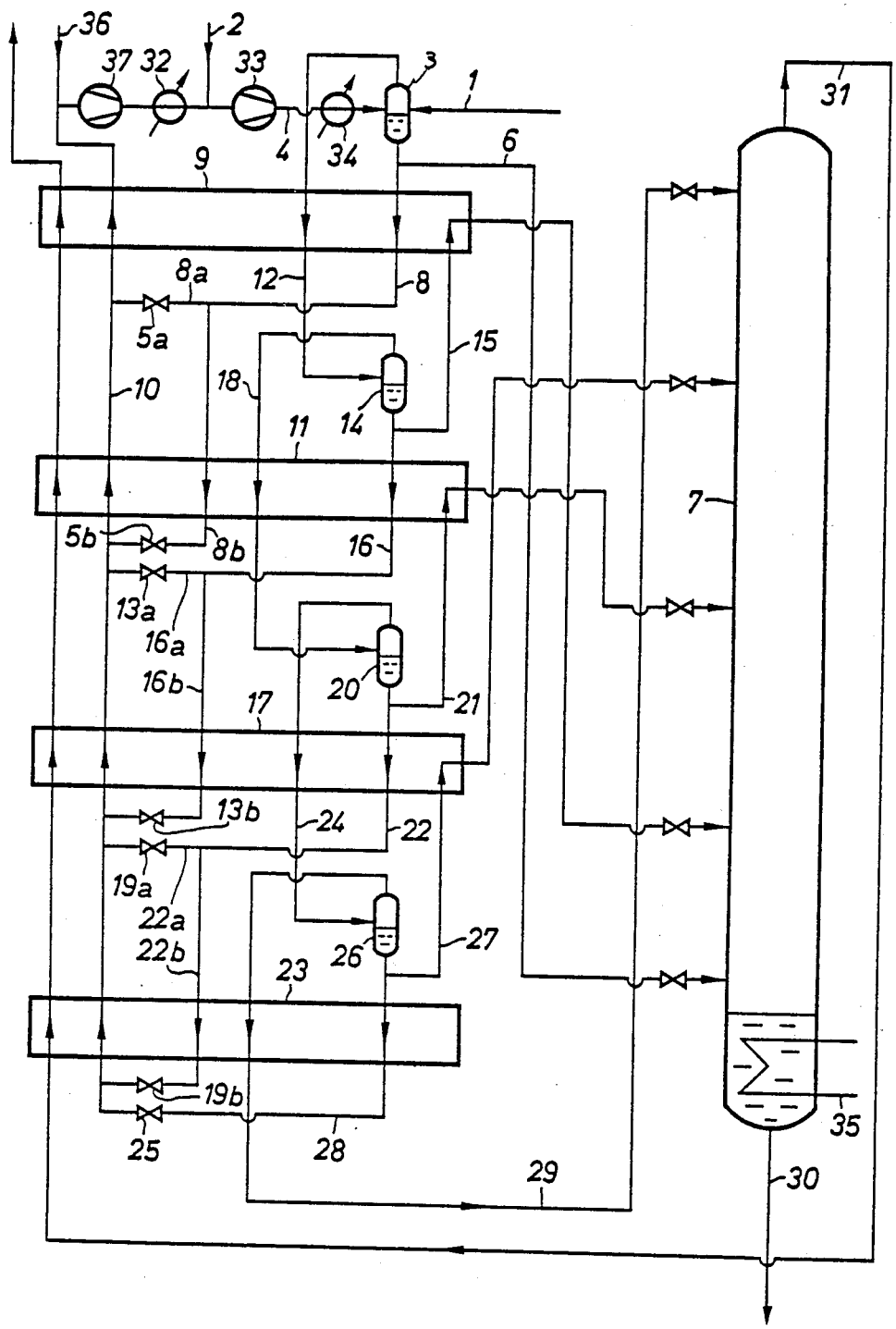

SEPARATION OF ETHANE AND HIGHER HYDROCARBONS FROM NATURAL GAS

BACKGROUND OF THE INVENTION

This invention relates to a process for separating $C_{2+}$ hydrocarbons from high pressure natural gas by rectification wherein the temperature and pressure values required for rectification are obtained by heat exchange and expansion, and wherein the resultant condensates from the expansion are introduced into a rectifying column.

A process of this type is described in U.S. Pat. No. 3,292,380. In this process, the natural gas is first cooled by heat exchange with cold rectified product, thus obtaining the readily condensible components in the liquid phase; a portion of the condensate is expanded and then introduced into the rectifying column. The components of the natural gas remaining in the gaseous state after said heat exchange are engine-expanded in an expansion turbine to the pressure of the rectifying column, thereby providing refrigeration for the process.

Frequently, cooling in heat exchange with cold product gas is insufficient so that additional external refrigeration is required, such as, for example, a propane or propylene cycle. In such a refrigerant cycle, losses of refrigerant occur, which in turn must be compensated for by adding more refrigerant. Another disadvantage of the conventional process is that it cannot be utilized with natural gas that contains significant quantities of carbon dioxide unless the $CO_2$ is separated from the natural gas in a special preliminary process step. Otherwise there would be the danger that solid precipitants are formed in the parts of the apparatus operated at low temperatures and/or with high $CO_2$ concentrations, and in some cases even complete blockage of conduits, etc. resulting in shutdown could occur. Finally, whereas the use of an expansion turbine is conventional, it is expensive equipment both with respect to initial investment and operating costs.

SUMMARY

Therefore, it is an object of one aspect of the present invention to provide a process of the aforementioned type having substantially none of the above-described deficiencies, and having reduced operating expenses and initial investment costs, while obtaining higher yields of ethane for natural gases poor in ethane.

Upon further study of the specification and appended claims, further objects and advantages of this invention will become apparent to those skilled in the art.

These objects are attained according to an aspect of this invention by a process using, for cold production, an open mixture cycle with multistage fractional condensation and by introducing part of the thus-obtained condensates into the rectifying column to produce the $C_{2+}$ hydrocarbons and recirculating the other part of these condensates to provide the required cold. An open mixture cycle is defined as a cycle used for refrigeration purposes wherein a mixture of components is employed as the refrigerant cycle medium and wherein the cycle medium is continuously being replenished by additional components to make up for condensate being continuously withdrawn from the cycle medium. The cycle medium in the present invention is compressed, condensed, expanded through valves, and then vaporized, the latter step absorbing heat in the conventional manner. The multistage fractional condensation used in connection with the open mixture cycle makes it possible to produce liquids serving to provide the required cold as well as for the actual separation of the $C_{2+}$ hydrocarbons. In this way, the same phase separators are utilized for cold production and for the separation of $C_{2+}$ hydrocarbons. The fresh feedstock is directly introduced into the open mixture cycle. The pressure of the natural gas feed can range between 1 and 60 bar. Depending on the pressure and quality of the natural gas and on the operating expenses, the number of stages in the multistage condensation generally ranges between 2 and 10, preferably between 2 and 5.

The temperature of the head product from the rectifying column is determined by the desired ethane yield and purity. For example, a mixture of methane with 1% ethane has a dew point at 45 bar of about 190 K. A mixture of methane with 5% ethane has a dew point of about 200 K at 45 bar. For a fixed ethane recovery and methane impurity, the ethane concentration, and hence the head temperature, is fixed by the overall mass balance. The lowest required temperature of about 190 K is not obtained, as in the conventional method, by turbine expansion; rather, it is obtained by the use of an open refrigeration cycle.

Consequently, when employing the process of this invention, the need for an expansion engine, e.g., turbine, and additional means for producing external cold are eliminated. Moreover, the process of this invention can also be utilized in connection with natural gases exhibiting relatively high $CO_2$ contents, e.g., 0.5 to 5.0 preferably 0.5 to 2% $CO_2$ by volume.

In a process using an expansion turbine for cold production, the outlet temperature of the turbine is usually much lower than the temperature of the head of the column (that is fixed by the required ethane recovery and methane impurity). The low temperature at the expander outlet, which can lead to freezing of $CO_2$ etc., is a consequence of the high pressure ratio of the machine which, in turn, is determined by the cold requirements of the process at low temperatures.

In a further aspect of this invention, a partial stream from the first condensate is conducted directly to the rectifying column. However, to-be-rectified partial streams from the downstream condensates are first heated in heat exchange with the to-be-recirculated partial condensate stream and the uncondensed fluid obtained in the respectively preceding condensation stage. This method of operation of the process provides highly efficient utilization of the produced cold, whereby the necessity for external refrigeration is eliminated. The condition of the resultant heated to-be-rectified partial streams can be vapor, liquid, or two-phase depending on the enthalpy-temperature profiles in the heat exchangers and the conditions in the rectifying column.

According to a further aspect of the process of this invention, the partial streams of condensates serving for cold production after being pressure-reduced and vaporized in heat exchange means, are compressed in one or several stages, and subjected again to condensation together with fresh feedstock. With multistage compression, the pressure reduction (expansion) of the partial streams of condensates can advantageously be effected only down to a pressure lying directly above (e.g., not more than about 0.1 bar above) the intake pressure of a second compressor stage. By this manner of operation, the volume of vapor produced during expansion is reduced whereby the energy requirement of the facility is decreased. Compression takes place in total to the pressure of the natural gas and/or to the inital pressure required for production of cold, corresponding at least to the operating pressure of the rectifying column.

Advantageously, the partial streams are cooled in heat exchange with the partial stream of condensate obtained in the respectively subsequent condensation stage and to be fed to the rectifying column, expanded, heated, and then compressed. According to another embodiment of the process, it is also possible to further cool the partial streams, after the initial, above-described cooling, in heat exchange with the to-be-rectified partial stream of condensate obtained in the respectively next but one downstream condensation stage and to expand, heat, and then compress these partial streams. (By next but one is meant not the immediately next downstream condensation stage but the one thereafter). Cooling is provided for the purpose of keeping the vapors produced during expansion at a minimum. The loss of available energy ('exergy') during expansion of a fluid in an adiabatic valve depends largely upon the volume change during expansion. It is therefore advantageous to expand sub-cooled liquid rather than vapor since the volume change on expansion is much less.

The heat produced during the subsequent compression step can be utilized, according to another aspect of the process, for heating the sump of the rectifying column. This is done preferably by heat exchange with hot compressed gas from the outlet of the first or second compressor stage.

To be able to produce the required refrigeration, the natural gas must meet certain conditions. On the one hand, the natural gas should have a high proportion of heavy gases and, on the other hand, should be under a high pressure. These conditions are not met in all cases. If the natural gas is present with a lower pressure, i.e., for example, between 1 and 30 bar, then it must be brought to an increased pressure of up to 60, preferably at least 40 bar, before being fed to the first condensation stage. These minimum pressures will be equivalent to the pressure in the rectifying column. This is accomplished advantageously in accordance with the invention by compressing the natural gas together with the recirculated vaporized partial condensate streams. In this embodiment, the feedstock natural gas depending on its pressure is fed to an appropriate compressor stage. This version is utilized, in particular, with low pressure natural gas having a low methane content, and high content of $C_{2+}$ hydrocarbons. For example, a natural gas with less than 50% methane, preferably 30 to 50% methane and more than 50% $C_{2+}$ hydrocarbons, preferably 50 to 70% by volume $C_{2+}$ hydrocarbons.

In contrast thereto, if the natural gas is initially present under elevated pressure (i.e. a pressure of between 30 and 60 bar), but has an only low proportion of $C_{2+}$ hydrocarbons, then another aspect of this invention is to provide a stage connected upstream wherein the $C_{2+}$- poor natural gas is enriched with $C_{2+}$ hydrocarbons by separating methane. This can be done conventionally, for example in a pressure swing adsorption installation or by a membrane process. With the use of a pressure swing adsorption installation, gases enriched with $C_{2+}$ hydrocarbons are produced under a low pressure which are then compressed together with the partial streams of condensate.

Accordingly, by using the process of this invention, all types of natural gases can be treated for the separation of $C_{2+}$ hydrocarbons so long as the natural gas in either its natural or modified state has prior to addition to the open mixture cycle a pressure as indicated above, and a volume concentration of at least 30%, preferably 30% to 50% methane, and at least 50%, preferably 50% to 70% $C_{2+}$ by volume.

A high concentration of $C_{2+}$ components is required in the feed gas in order to obtain efficient operation of the open mixture cycle used for cold production. A low $C_{2+}$ and high methane content of the feed gas results in an excessive recycle ratio in the open mixture cycle in order to provide the cold requirements of the process.

BRIEF DESCRIPTION OF DRAWING

The attached drawing is a preferred comprehensive embodiment and example of the invention set forth in schematic form and embodying four condensation stages.

DETAILED DESCRIPTION

By way of conduit 2, fresh feedstock is introduced under a pressure of 6 bar and at a temperature of 290 K. This feedstock is a natural gas which has been previously enriched with $C_{2+}$ hydrocarbons, thereby resulting in the following composition:

| $CH_4$ | 40% |
|---|---|
| $C_2H_6$ | 30% |
| $C_{3+}HC$ | 30% |

This enriched natural gas is mixed with the cycle gas (described in greater detail below) which has been compressed in a compressor 37 to 6.5 bar, and the mixture is compressed in a compressor 33 to a pressure of 40 bar. This resultant high pressure gas is then cooled in cooler 34 to 310 K, and the resultant condensate, enriched with heavy components, is obtained in phase separator 3. One part of this condensate, about 1 to 10% is introduced via conduit 6 at the bottom of a rectifying column 7. The introduction of this partial stream, and the others to be introduced as described infra is effected at locations adapted to the equilibrium conditions in the rectifying column 7 and to the respective compositions of the partial streams to be introduced. The other part of the condensate withdrawn via conduit 8, after being cooled to about 270 K in a heat exchanger 9, is then expanded to a pressure of about 6.5 bar into a collection conduit or manifold 10. This can take place either directly via conduit 8a with valve 5a and/or, after additional cooling to about 230 K in a heat exchanger 11, via conduit 8b with valve 5b.

The fraction in phase separator 3 that has remained in the gaseous phase during cooling and is enriched with light components is withdrawn via conduit 12, cooled to about 270 K in heat exchanger 9, and fed into a phase separator 14. A partial stream of the condensate, e.g., about 5 to 15%, obtained during this step at a temperature of about 270 K is withdrawn via conduit 15 and, after being heated to about 290 K in heat exchanger 9, fed into the rectifying column 7. The other partial stream is conducted via conduit 16, after being cooled to about 230 K in heat exchanger 11, to the collection manifold 10, either directly via conduit 16a with valve 13a and/or, after additional cooling to about 210 K in a heat exchanger 17, via conduit 16b with expansion valve 13b.

The remaining gaseous components are withdrawn via conduit 18, cooled in heat exchanger 11 to about 230 K, and passed on to the subsequent condensation stage, i.e. fed into a separator 20. In the above-described manner, a partial stream of the condensate, e.g., 5 to 15%, obtained with a temperature of about 230 K, is withdrawn via conduit 21, heated in heat exchanger 11 to a temperature of about 250 K, and introduced into the rectifying column 7. The other partial stream is withdrawn via conduit 22 and, after cooling to about 210 K in heat exchanger 17, conducted either via conduit 22a with valve 19a directly and/or, after additional cooling to about 190 K in a heat exchanger 23, via conduit 22b with valve 19b into the collection manifold 10.

The still remaining gaseous fraction is removed via conduit 24 and fed into a separator 26. Via conduit 27, a partial stream of condensate, e.g., about 10 to 20%, obtained at a temperature of about 210 K is withdrawn, heated in heat exchanger 17 to about 220 K, and fed into the rectifying column 7.

The other partial stream is withdrawn via conduit 28 and, after cooling to about 190 K in heat exchanger 23 and expansion 25, introduced into the collection manifold 10. The fraction of the natural gas that has finally remained in the gaseous stage is almost pure methane with a low proportion, e.g., less than 5 volume %, of $C_{2+}$ components and is withdrawn via conduit 29 and, after being cooled to about 190 K in heat exchanger 23, introduced to the upper region of the rectifying column.

The rectifying column 7, having about 20 theoretical plates, is operated under a pressure of 38 bar, and has an operating temperature range of between about 190 K at the head and about 300 K at the sump. The sump of the column is heated by means to be described below. A practically methane-free, e.g., less than 1 mol % methane, $C_{2+}$ fraction accumulates in the sump and is removed via conduit 30 whereas residual gases are obtained overhead via conduit 31 which contain only minor proportions of hydrocarbons with 2 or more carbon atoms, e.g., less than 5 volume % $C_{2+}$.

These residual gases, obtained at a temperature of about 190 K, are conducted, to utilize their refrigeration values, via heat exchangers 23, 17, 11, and 9, and heated to a temperature of about 305 K and discharged.

The partial streams of condensates, combined in collection conduit 10, are available, after passing through heat exchanger 9, at a temperature of about 305 K and under a pressure of about 1.1 bar and are compressed, in a first compressor 37, to about 6.5 bar. The thus-generated heat is removed by means of a heat exchanger 32. After further compression in compressor 33 to about 40.5 bar and cooling in heat exchanger 34, the condensates are subjected, via conduit 4, to the first condensation stage in the manner described above.

The heat generated during compression is utilized in accordance with this invention either directly or via a heat transfer fluid for heating means 35 of the sump of the rectifying column 7. This can take place by means of heat exchangers 32, 34, and 35, or by way of parallel-connected heat exchangers, not shown.

Furthermore, natural gas under low pressure can be combined with the partial condensate streams in collection manifold 10 via conduit 36 upstream of the first compressor and/or natural gas under high pressure can be introduced via conduit 1 into the phase separator 3.

In place of the collection manifold 10, it is also possible to choose a collection conduit, not shown, wherein the ambient pressure is just above (e.g., not more than about 0.1 bar above) the intake pressure of compressor 33. The condensates obtained in separators 3, 14, 20, and 26 can, in this case, be expanded to a higher pressure into the collection conduit, not shown. By this process variant, the amount of vapor produced during expansion is reduced whereby the energy requirement of the entire installation is decreased.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a process for the separation of $C_{2+}$ hydrocarbons by rectification of natural gas under elevated pressure, the improvement which comprises passing the natural gas feedstock into an open mixture cycle fluid medium, said feedstock having a pressure of over 30 bar up to 60 bar and a volume concentration of at least 30% methane and at least 50% $C_{2+}$, subjecting the resultant mixture to multistage fractional condensation, passing one part of the resultant condensates into a rectifying column to separate the $C_{2+}$ hydrocarbons and recirculating the other part of the condensates in the open mixture cycle providing the total cold values for the process, and wherein a partial stream of the first condensate of the multistage fractional condensation is conducted directly to the rectifying column, and at least one of the to-be-rectified partial streams of the downstream condensates, prior to rectification, is heated in exhange with a to-be-recirculated partial condensate stream obtained in the respectively preceding condensation stage.

2. A process according to claim 1, wherein the to-be-recirculated partial streams of condensates, serving for cold production, are, after expansion and heat exchange, compressed in at least one stage, and the compressed partial streams of condensates in the vapor state are subjected to condensation together with fresh feedstock.

3. A process according to claim 1, further comprising compressing fresh natural gas feedstock prior to condensation, to at least the operating pressure of the rectifying column.

4. A process according to claim 3, wherein the fresh natural gas feedstock is compressed from a pressure below 30 bar to a pressure above 30 bar.

5. A process according to claim 3, wherein the pressure of the compressed gas is 40 to 60 bar.

6. A process according to claim 3, wherein the fresh natural gas feedstock is compressed together with the partial streams of condensates of the open cycle fluid medium.

7. A process according to claim 6, wherein the fresh natural gas feedstock is compressed from a pressure below 30 bar to a pressure above 30 bar.

8. A process according to claim 4, wherein the pressure of the compressed gas is 40 to 60 bar.

9. A process according to claim 1, wherein the rectifying column has a sump and further comprising heating said sump of the rectifying column in heat exchange with hot, compressed gas.

10. A process according to claim 4, wherein the rectifying column has a sump and further comprising heating said sump of the rectifying column in heat exchange with hot, compressed gas from said compressing step.

11. A process according to claim 1, further comprising a stage upstream comprising enriching natural gas to the desired value of $C_{2+}$ hydrocarbons.

12. A process according to claim 11, comprising conducting the enriching by passing the natural gas through a pressure swing adsorption facility to selectively deplete the gas in methane.

13. A process according to claim 1 wherein a plurality of the to-be-rectified partial streams of the downstream condensates, prior to rectification, are heated in heat exhange with to-be-recirculated partial condenstate streams obtained in the respectively preceding condensation stage.

14. A process according to claim 13 wherein said plurality of to-be-rectified partial streams constitutes all of said to-be-rectified partial streams of the downstream condensates.

* * * * *